United States Patent [19]

Nguyen

[11] Patent Number: 5,389,789
[45] Date of Patent: Feb. 14, 1995

[54] PORTABLE EDGE CRACK DETECTOR FOR DETECTING SIZE AND SHAPE OF A CRACK AND A PORTABLE EDGE DETECTOR

[75] Inventor: Donald D. Nguyen, Lawrenceville, N.J.

[73] Assignee: Union Camp Corporation, Princeton, N.J.

[21] Appl. No.: 886,053

[22] Filed: May 20, 1992

[51] Int. Cl.⁶ ............ G01N 21/89; G01N 21/86
[52] U.S. Cl. ............... 250/341.1; 250/349; 250/359.1; 250/571; 250/572
[58] Field of Search ............ 250/341, 572, 571, 359.1, 250/349; 356/430

[56] References Cited

U.S. PATENT DOCUMENTS

| | | | |
|---|---|---|---|
| 2,735,329 | 2/1956 | Meunier | 88/14 |
| 3,781,115 | 12/1973 | Rader et al. | 356/167 |
| 3,859,538 | 1/1975 | Mannonen | 250/359.1 |
| 3,906,232 | 9/1975 | Meihofer | 250/341 |
| 4,160,913 | 7/1979 | Brenholdt | 250/563 |
| 4,247,204 | 1/1981 | Merlen et al. | 356/431 |
| 4,265,545 | 5/1981 | Slaker | 250/572 |
| 4,302,105 | 11/1981 | Sick | 250/572 |
| 4,335,316 | 6/1982 | Glanz et al. | 250/572 |
| 4,559,451 | 12/1985 | Curl | 250/560 |
| 4,591,726 | 5/1986 | Schenk | 250/572 |
| 4,652,124 | 3/1987 | Bowen et al. | 356/237 |
| 4,680,806 | 7/1987 | Bolza-Schunemann | 382/65 |
| 4,709,157 | 11/1987 | Shimizu et al. | 250/572 |
| 4,728,800 | 3/1988 | Surka | 250/572 |
| 4,788,442 | 11/1988 | Sabater et al. | 250/572 |
| 4,791,304 | 12/1988 | Iida | 250/563 |
| 5,019,710 | 5/1991 | Wennerberg | 250/359.1 |
| 5,047,640 | 9/1991 | Brunnschweiler et al. | 250/341 |
| 5,068,799 | 11/1991 | Jarrett, Jr. | 356/430 |
| 5,166,536 | 11/1992 | Rye | 250/572 |
| 5,260,583 | 11/1993 | Rye | 250/572 |
| 5,289,007 | 2/1994 | Hergert | 250/341 |

Primary Examiner—Carolyn E. Fields
Attorney, Agent, or Firm—Woodcock Washburn Kurtz Mackiewicz & Norris

[57] ABSTRACT

A detector for detecting edge cracks in the web in a papermaking machine includes a plurality of light sources for directing light at the web and a plurality of light sensors for receiving the light through the cracks for generating a plurality of signals indicative of the dimensions and shape of the crack. The size and shape of the cracks are determined from the sensor outputs by a processor and preferably displayed on a suitable display. Crack shapes are determined by introducing a delay parameter which relates the output for each detector channel to the time a first detector channel is triggered. In particular, the first detector channel which is triggered is given a delay value of zero, while other channels are given delay values greater than zero depending on the order of activation. The signal acquisition and analysis are designed to be compatible with a personal computer so as to ensure the system's portability. The device also includes the use of fiber optics and quick response infrared sensors to meet the high resolution and high temperature conditions for crack detection in a papermaking machine, for example. Plural light sources and sensors detect an edge of a moving paper web when a sensor detects light on at least two different occasions during a gap time of duration such that light detection may be assured to be caused by sheet flutter or wander rather than edge cracks.

27 Claims, 10 Drawing Sheets

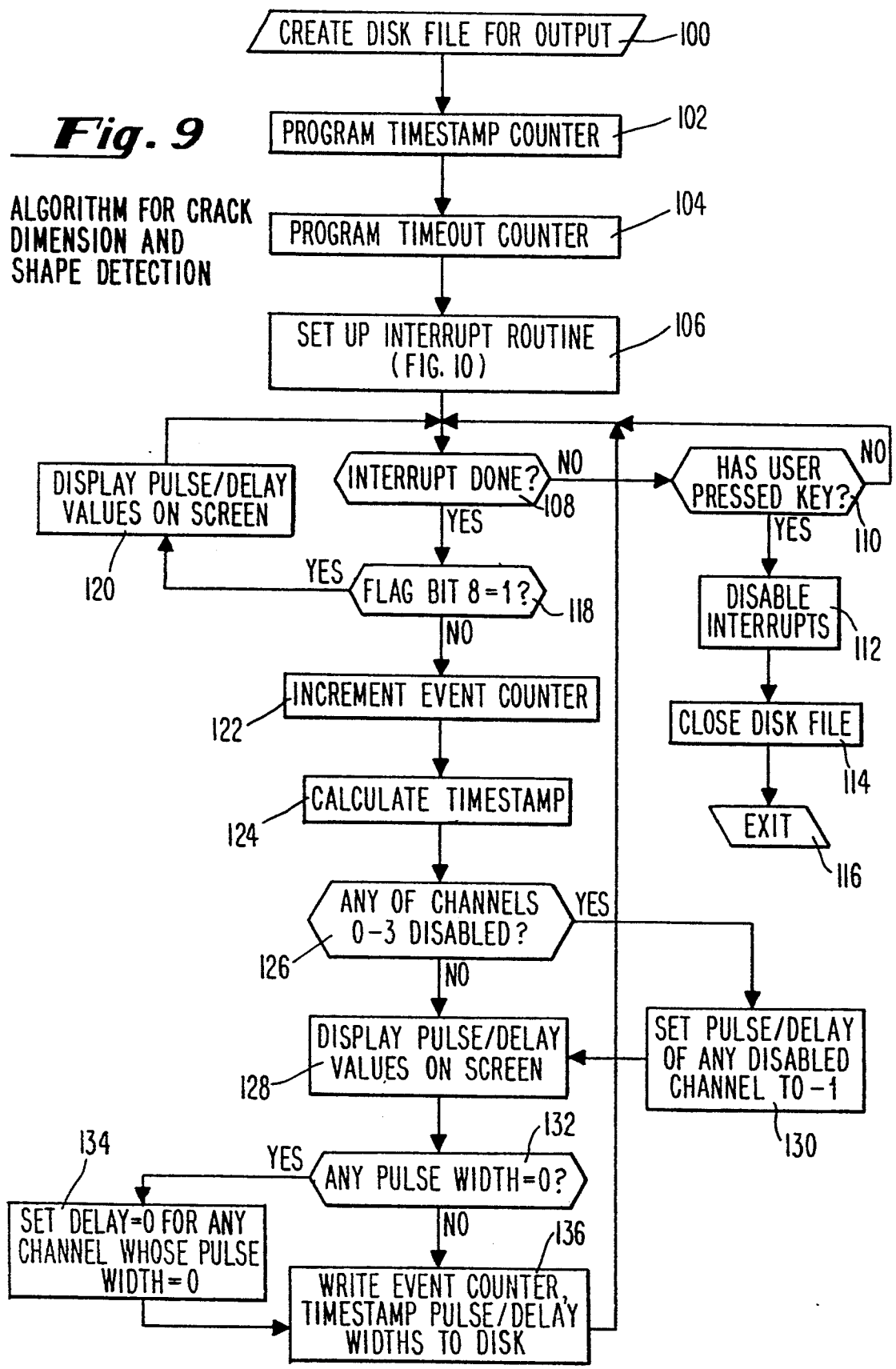

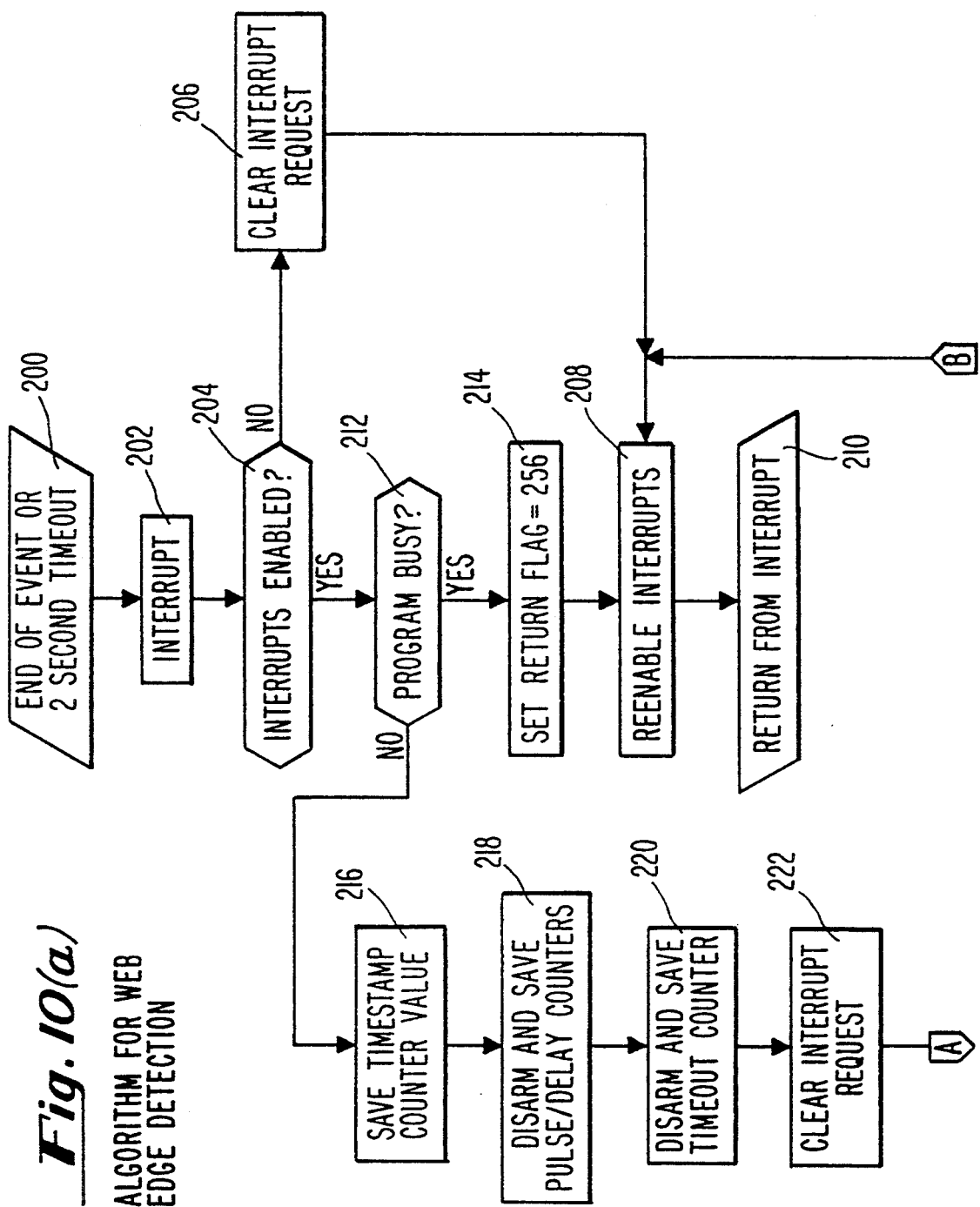

PORTABLE EDGE CRACK DETECTOR FOR DETECTING SIZE AND SHAPE OF A CRACK AND A PORTABLE EDGE DETECTOR

BACKGROUND OF THE INVENTION

1. FIELD OF INVENTION

This invention pertains to a detector used for sensing cracks in an elongated web, and in particular, to a detector for detecting the size and shape of edge cracks in a paper web in a papermaking process.

2. BRIEF DESCRIPTION OF THE PRIOR ART

Most paper today is made in a continuous sheet on large papermaking machines from a web which undergoes several processing steps. The web is usually 20 feet wide or greater and is made in a continuous manner at very high speeds of, for example, 3000 ft/min. Because the profitability of papermaking machines is directly related to their continuous operation, interruption of full production is extremely costly and, therefore, factors which cause such interruptions are studied intensely to reduce such incidents to a minimum. One factor which results in the interruption of the papermaking machine is a crosswise tear in the paper web. Whenever such a tear occurs the papermaking machine must be shut down totally or partly until the problem is resolved. One cause of these tears are cracks formed at the web edges as the web travels through the machine. While often minor cracks can be tolerated with no problems, larger cracks can propagate across the sheet to form a tear.

Therefore, it is important to monitor cracks on the web edges and to analyze their formation and behavior in a papermaking machine to control web tearing. A better understanding of crack formation and propagation would also lead to improved preventive maintenance and emergency procedures. In fact, numerous devices are known for detecting cracks in moving elongated webs for such purposes. For example, devices are known which scan the web material in the direction of its width to find cracks as taught in U.S. Pat. No. 4,160,913 to Brenholdt, U.S. Pat. No. 4,247,204 to Merlen et al., U.S. Pat. No. 4,335,316 to Glanz et al. and U.S. Pat. No. 4,791,304 to Iida. Other devices are also known which detect tears and holes as well as web edges using stationary light transmission/detection systems. In these systems, light is transmitted toward the web material and is detected by detectors on the other side of the web material when the light is allowed to pass through the web material by cracks or holes therein. For example, such devices are taught in U.S. Pat. No. 2,735,329 to Meunier (sheet metal), U.S. Pat. No. 4,559,451 to Curl, U.S. Pat. No. 4,652,124 to Bowen et al. U.S. Pat. No. 4,680,806 to Bolza Schunemann, U.S. Pat. No. 4,709,157 to Shimizu et al., U.S. Pat. No. 4,728,800 to Surka and U.S. Pat. No. 4,788,442 to Sabater et al.

The above-mentioned devices detect tears in fabric webs which are relatively thick and move at relatively slow running speeds. Until now, because of the high speed of papermaking machines and the resultant flutter of the edges of the light weight paper sheets, it has been very difficult to sense and monitor edge cracks properly. Moreover, such systems do not determine the size and shape or direction of cracks in such a manner that tears in the web can be more accurately predicted. The present invention is designed to improve performance by determining the size and the shape of cracks in the web even in the presence of sheet flutter.

SUMMARY OF THE INVENTION

In view of the above, the most important objective of the present invention is to provide a detector which can be used to sense edge cracks in a paper web accurately even in the presence of significant machine disturbances such as sheet edge flutter and sheet edge lateral movement.

A further objective is to provide a detector which is relatively small which can be moved easily along the sheet edge from one part of a papermaking machine to another. This capability is very important in case it is necessary to identify and fix the machine sections which generate edge cracks Another objective of the invention is to keep the device operating at high humidity and temperature conditions, such as in a paper machine dryer, where ambient conditions can be up to 200° F. at near saturating humidity. Yet another objective of the invention is to provide a detector which can be easily interfaced with a personal computer to ensure the system portability. The amount of data collected must be minimized since it is restricted by the data processing rate of the personal computer.

A further objective of the present invention is to provide an edge detector in which the crack dimensions such as width and length of an edge crack and the crack shape can be determined from a single measurement. Crack widths and lengths are defined as the dimensions of the crack openings along the machine direction and the cross-machine direction, respectively. Cracks can adopt various shapes depending on the general orientation such as slanting toward or against the sheet running direction or both to have a crooked slope, and by detecting such shapes, those cracks with shapes more likely to cause a tear can be determined.

Yet another objective is to provide an edge crack detector which requires minimum data processing, thereby obviating the need for high-speed and expensive processors which are not appropriate for portable equipment.

A yet further objective of the present invention is to provide an edge crack detector which can function without the need for tracking or compensating for lateral drifts or flutter of the paper web.

As known to those skilled in the art, the paper web formed in a papermaking machine is generally subject to two kinds of extraneous movements: flutter and lateral drift. Flutter refers to a three dimensional movement of the web similar to the movement of a flag in a breeze. Lateral drift refers to the movement of the web transverse to the machine direction. An edge crack detector deployed along a papermaking line must be able to detect the edge movement caused by either flutter or lateral drift. It is desired to eliminate such problems from the edge determination.

Briefly, a detector for sensing edge cracks constructed in accordance with this invention consists of an array of light emitters preferably in the infrared region and a matching array of IR-sensitive receivers for detecting the light. The emitters and receivers are positioned on the opposite sides of the web so that only the light transmitted through the cracks is detected by the receivers The receivers are spaced laterally in the cross-machine direction from the web edge and are oriented so that each generates a signal related to the width of the crack at a particular distance from the edge of the web. The signals from the receivers are then fed to a signal processor for determining the crack's dimensions and shape. Tracking means are also provided to detect and compensate for the lateral drift. In accordance with the invention, the tracking means may be implemented by manipulating the signals received in the signal processor.

By way of example, crack shape can be monitored by the addition of a parameter, the delay time D. The light transmitting/detecting first channel which is triggered is set to have a value of D equal to zero. Other channels have values of D greater than zero depending on the order of activation. In accordance with the invention a combination of the values of crack widths P and delay times D can be used by the signal processor to recreate the crack size and shape.

A method to detect the web edge in accordance with a preferred embodiment of the invention is to activate the IR-emitters in a preselected sequence and to feed the output of the receiver into the signal processor to detect sources which are blocked from the receiver by the web. In this manner, the instantaneous position of the web edge is obtained, including the profiles of edge cracks. Analog or digital filters may also be used to eliminate the effects of flutter or lateral drift.

Other objectives and advantages of the invention shall become apparent from the detailed description of the invention.

BRIEF DESCRIPTION OF THE FIGURES

FIGS. 9,10 (a)and 10(b) illustrate flow charts of the system for collecting and processing data on crack dimensions, shapes, and edge detection in accordance with the invention.

DETAILED DESCRIPTION OF THE INVENTION

Figure 1:
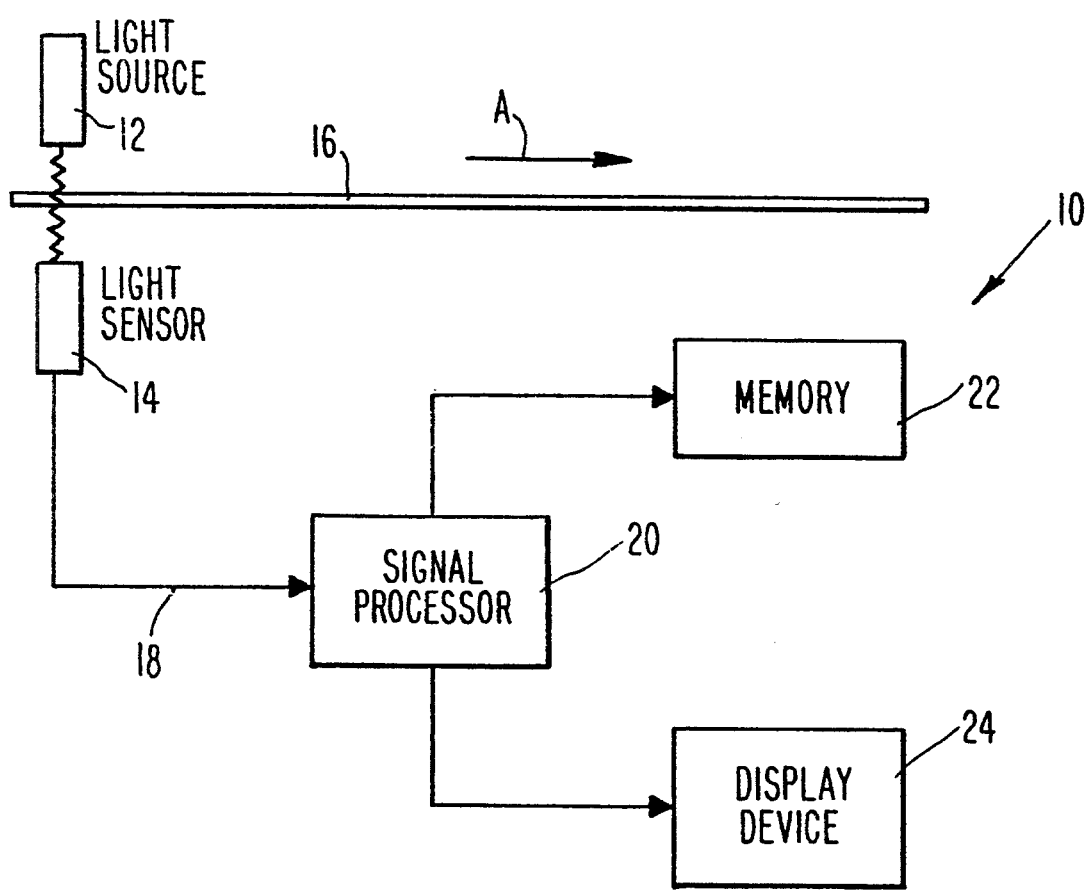
FIG. 1 shows a schematic diagram of a preferred embodiment of a portable edge crack detector constructed in accordance with this invention.

FIG. 1 illustrates a portable edge crack detector 10 constructed in accordance with this invention, including a plurality of sources of light 12 which respectively direct infrared light toward a plurality of infrared light sensors 14 across a paper web 16 moving at high speed in the direction indicated by arrow A so that at least some of the light may be blocked by the web. Light sensor 14 has an output schematically indicated by line 18 which is fed to a signal processor 20. The signal processor 20 analyzes this output 18 to detect the physical dimensions, such as the width, length, and shape of edge cracks on web 16 in accordance with the techniques of the invention. This information may be stored in a memory 22 and/or displayed on a display device 24. The display device 24 may be for example, a printer, a plotter, or a video display.

Figure 2:
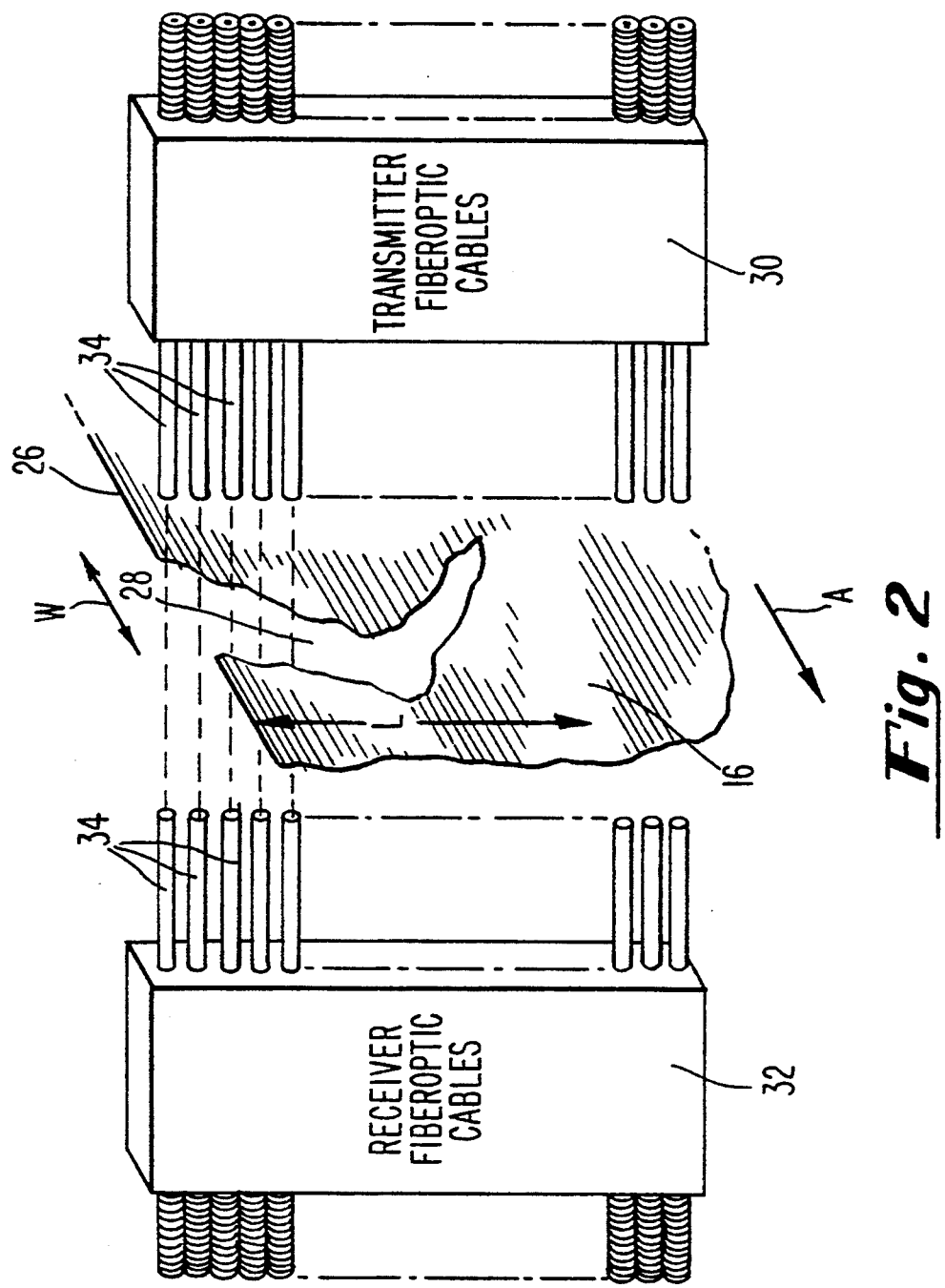
FIG. 2 shows an isometric view of the IR transmitters and receivers of FIG. 1 used for crack detection.

As shown in more detail in FIG. 2, web 16 runs in a papermaking machine in direction A with its edge 26 disposed between light sources 12 and light sensors 14. The edge 26 may have a crack 28 which typically has an irregular shape with a maximum length indicated by the letter L and a maximum width W. Light source 12 includes one or more IR crack detection transmitters 30 generating light in the range of 7.5–9 $\mu$m wavelength. This range is selected because frequently the air adjacent to the web has a very high humidity. Humid air is relatively transparent to IR light at this frequency so that it will not affect significantly the measurements made by the edge crack detector 10 of the invention.

The light detection transmitters 30 direct the IR light toward the light sensor 14 which preferably consists of one or more IR crack detection receivers 32. Each crack detection transmitter 30 and receiver 32 includes a plurality of needle tip fiber optic cables 34 with a diameter smaller than 1/16" as shown for respectively transmitting and receiving the IR light for crack detection. The tips of the fiber optic cables 34 are preferably in parallel and spaced about 0.25 inches apart. The receivers 32 cooperate with the transmitters 30 so that each receiver 32 monitors the width of an edge crack at a predetermined distance from the edge 26. Thus, the first crack detection receiver 32 may monitor the width of the gap about 0.125 inches from the edge, the second receiver may monitor the width of the gap at 0.375 inches from the edge and so on. Thus, by correlating the information from the individual receivers 32, a two-dimensional composite profile of the edge crack may be obtained. The number of receivers 32 to be used is determined by the maximum size of the cracks that are to be monitored. A system of this type is described in abandoned U.S. Pat. application Ser. No. 07/550,406, filed Jul. 10, 1990, by the present inventor, the contents of which are hereby incorporated by reference in their entirety.

As shown in FIG. 2, for a maximum crack length of 4.0"16 pairs of receiver-emitter fiber optic cables 34 may be needed. The receivers 32 and the transmitters 30 may both be, for example IR sensors F7M available from Scientific Technologies Inc. that have been modified to have response time reduced to 0.1 ms. Each of these sensors includes a source of light as well as a light detector connected to the fiber optics cables 34 having the characteristics and configurations described above. Also, the fiber optic cables are preferably of sufficient length to isolate the electric components from high ambient temperature and humidity.

The only elements of the detector described above which must be situated in the vicinity of the web are the compact fiber optics strands 34 used for conditioning the light sources and the received lights as shown in FIG. 2. These elements are relatively small and can withstand even the high temperature and humidity conditions of the paper machine along a papermaking line. Thus, the detection is portable along the papermaking line.

Figure 3:
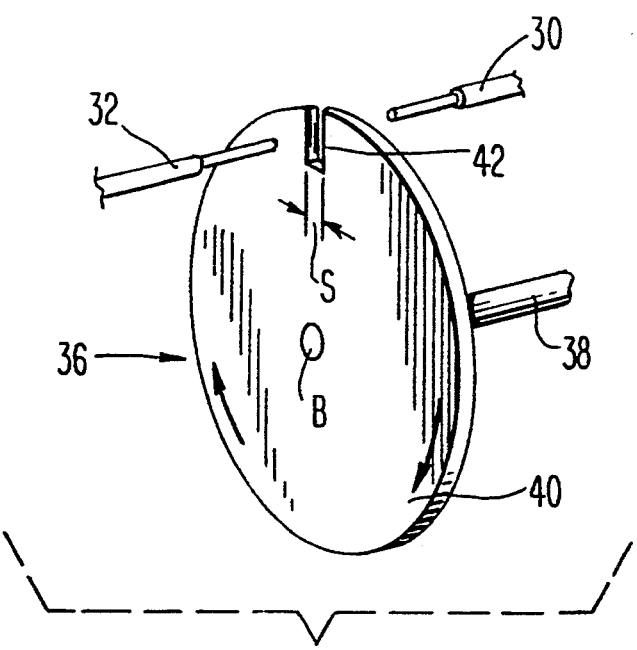
FIG. 3 shows an isometric view of a device for calibrating the detector of FIG. 1.
Figure 4:
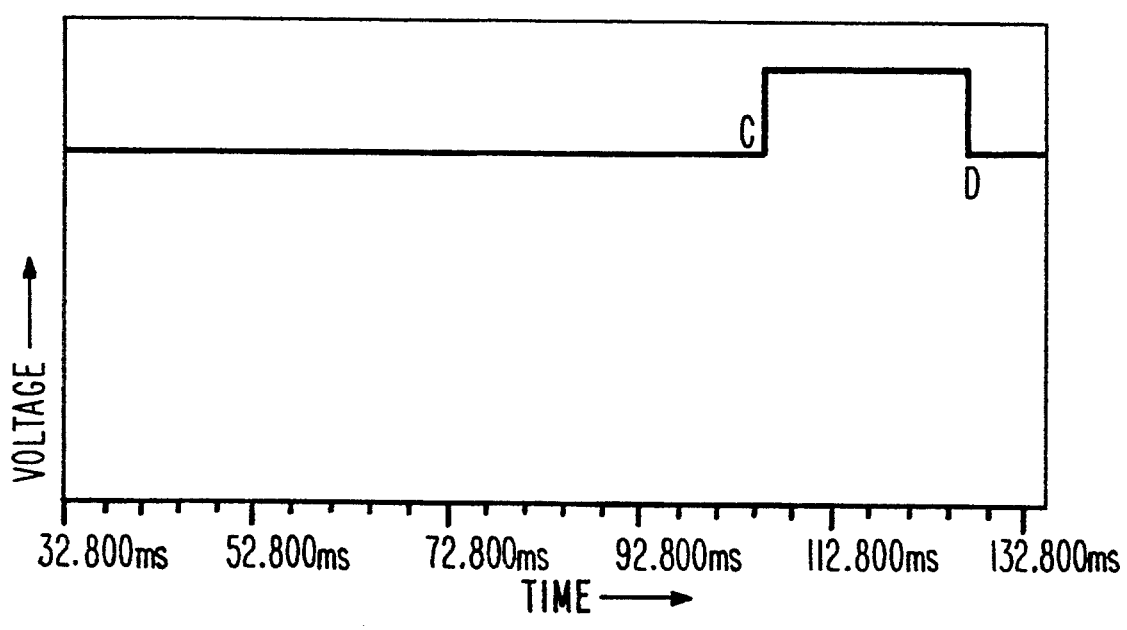
FIG. 4 shows a typical response curve by one pair of sensors for a crack detected by the apparatus of FIG. 1.

The response of pairs of IR transmitter/receivers made by different manufacturers may vary somewhat and, therefore, it may be necessary to calibrate them. A device 36 for calibrating a crack detection transmitter 30 and a crack detection receiver 32 is shown in FIG. 3. The device consists of a shaft 38 for rotating a thin wheel 40 as indicated by arrow B. A notch 42 is made in the wheel by making two parallel cuts substantially in the radial direction at a preselected spacing S apart and removing the material therebetween. The wheel is rotated at a high speed so that the notch 42 has a linear velocity equal to the speed of the web 16 in the papermaking machine. The transmitter 30 and receiver 32 are positioned across from each other close to the perimeter of the wheel 40, with the wheel 40 disposed in between. As shown in FIG. 3, the receiver is positioned with its slit extending perpendicularly to the notch 42. As the wheel 40 rotates, the light from the crack detection transmitter 30 is blocked from the crack detection receiver 32 except at the notch 42. The signal from the receiver is recorded, and the wheel 40 is changed for a different wheel having a notch with a different spacing S. Different wheels may be made with the spacing increasing in steps from 1/16 inch to 1.50 inches. A typical curve of the digital signal generated by the receiver for a notch is shown in FIG. 4 wherein the vertical axis indicates the signal voltage and the horizontal axis indicates time. It was found that the elapsed time between points C and D is proportional to the width of the notch 42. Thus, the device in FIG. 3 can be used to generate a calibration standard for an edge crack detector. This standard then may be used to determine the width of a crack from the signals generated by a receiver. Based on the response time of the detector, a maximum sensitivity of about ⅛ inches in crack width dimension at a web speed of 3000 ft/min. may be possible.

Figure 5:
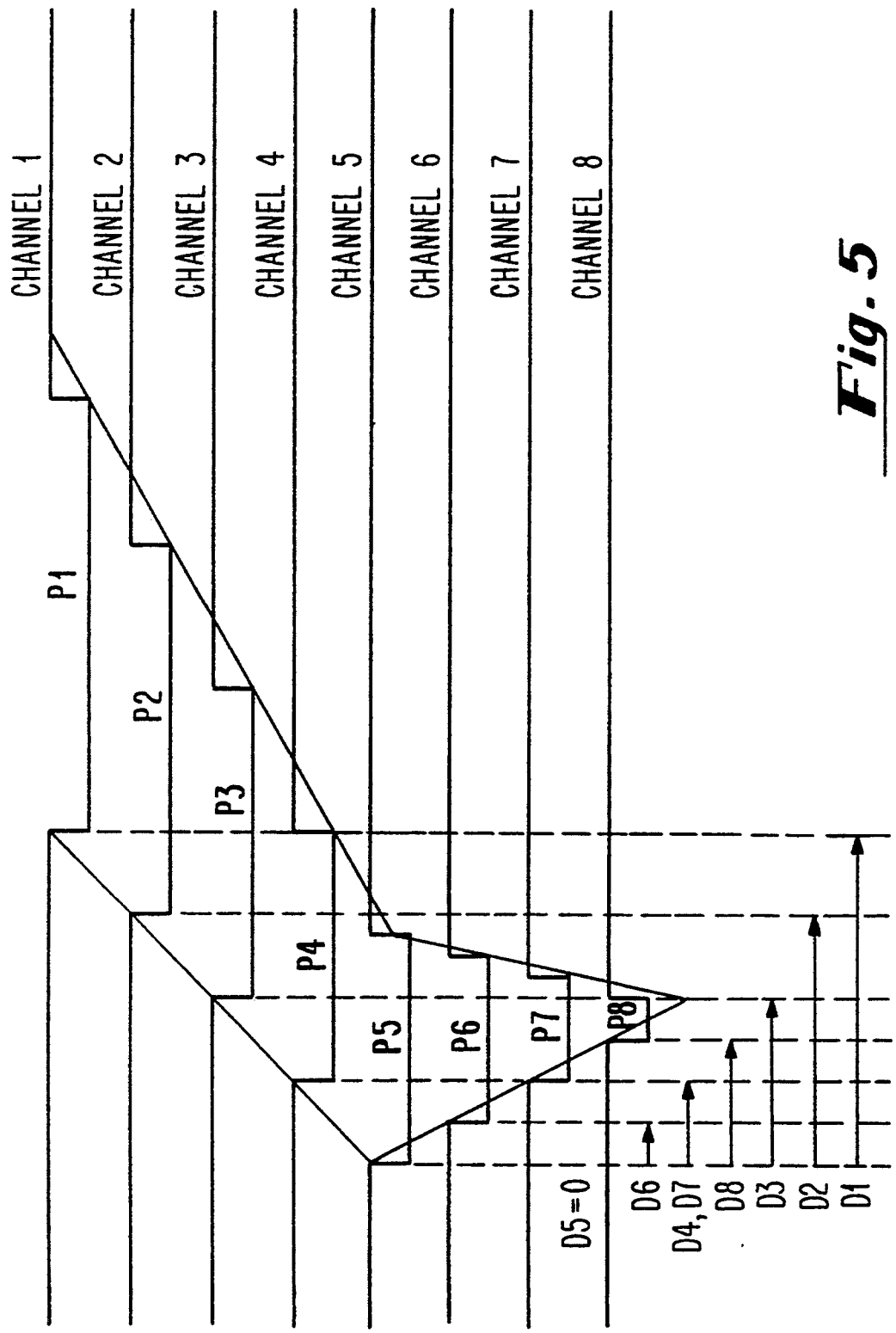
FIG. 5 is a diagram of data input to the program of the invention for calculating and displaying crack dimension and shape.

During operation of the circuit of the invention, a counter of signal processor 20 is used to track the outputs of sensors 14 for determining the size and shape of cracks 28 in the web 16. At the time a sensor 14 is activated, an internal clock of the counter is reset to zero. Between points C and D of FIG. 4, the counter is activated and counts up or down to register only the time interval between on and off, which corresponds to the crack width W indicated by that sensor channel. The time interval is coded by the count values (P values) as shown in FIG. 5. The amount of memory required per channel to store this data is only about 10 bytes or about 160 bytes for an array of 16 channels. This low memory requirement is an important feature to make the total system portable since any standard personal computer can be used to process the resulting data.

Since the sensor response time is tuned to 0.1 ms, the sensor resolution for the width W is the distance the web travels in 0.2 ms, or enough time to turn the sensor ON then OFF. For a web speed of 3000 fpm, the sensor resolution has been confirmed to be about 0.125".

The crack length L in the direction along the width (transverse to the moving direction) of the web 16 is equivalent to the number of channels that are triggered multiplied by 0.25" which is the distance in a preferred embodiment between two adjacent sensor channels. The crack length is thus measured by an increment of 0.25" in FIG. 5.

Figure 6:
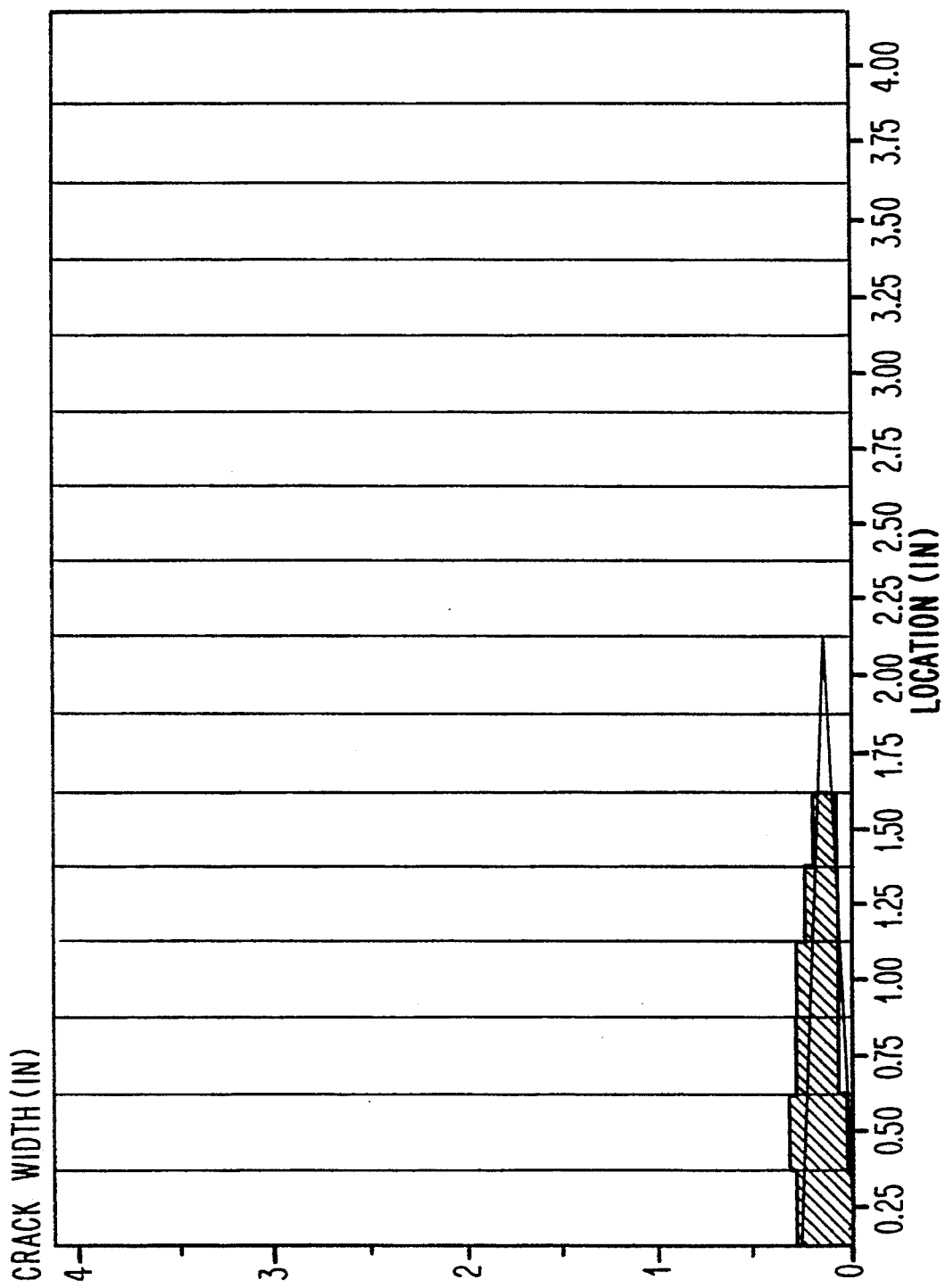
FIGS. 6–8 shows typical formats of the displayed output.
Figure 7:
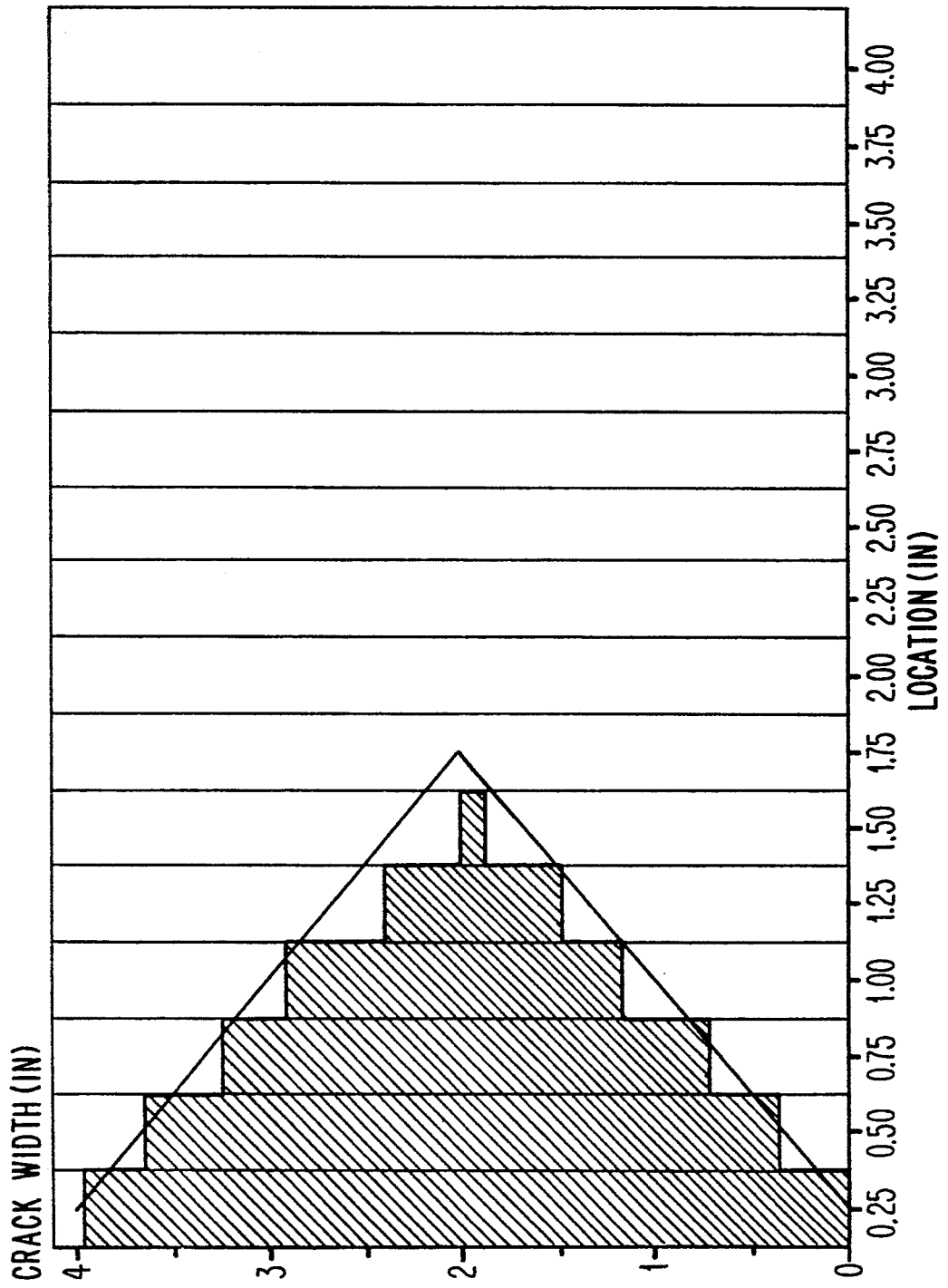
Figure 8:
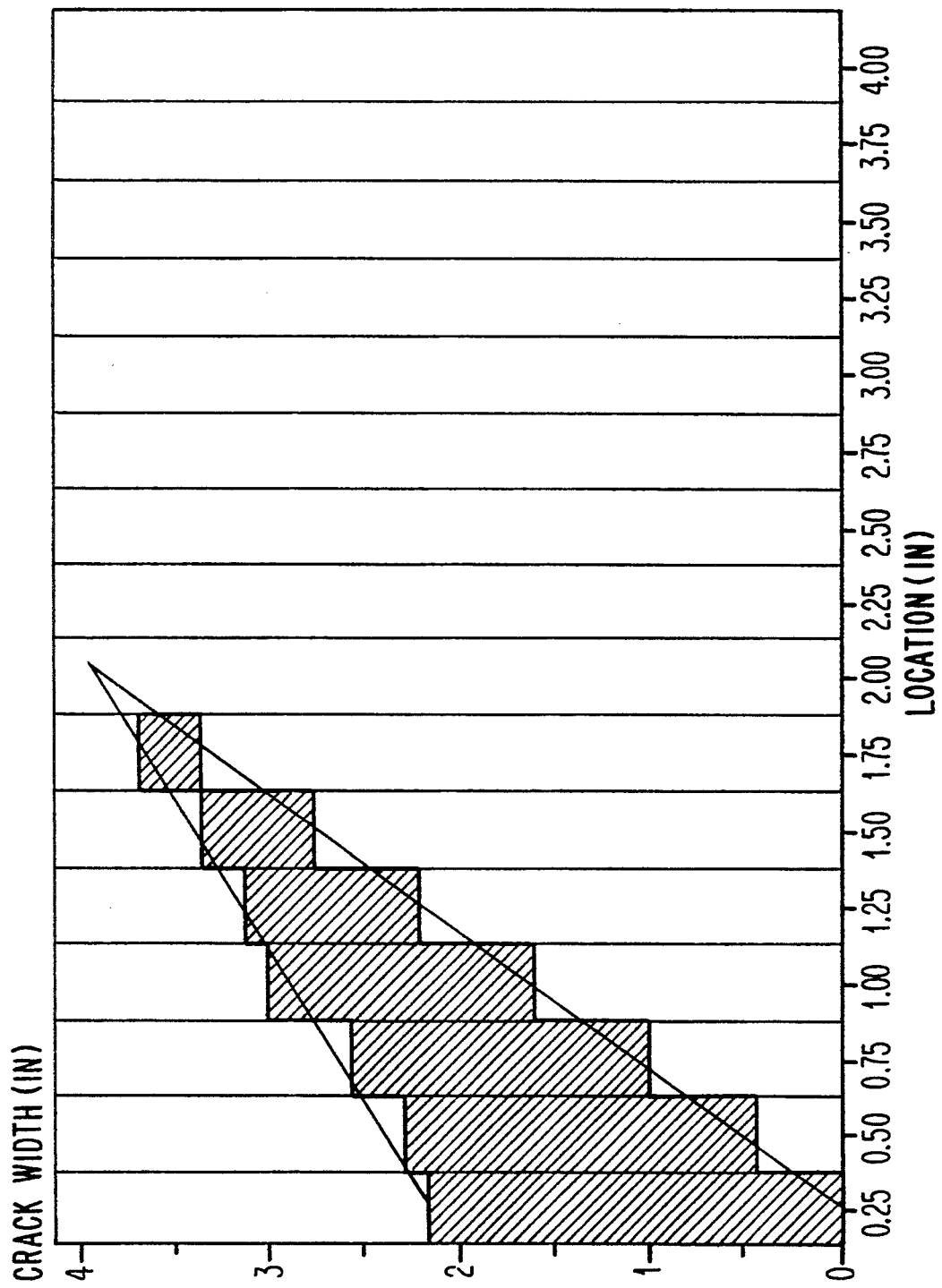

Crack shape can be monitored in accordance with the invention by the addition of a third parameter, the delay time D, as illustrated in FIG. 5. As shown, the first detector channel which is triggered is set to have a value of D equal to zero. Other channels have values of D greater than zero depending on the order of activation. These values are determined by processor 20 and stored for display on display device 24. A combination of the values of Ps and Ds can be used to recreate the crack size and shape as illustrated in FIGS. 6, 7 and 8, where the horizontal axis represents the output of each detector and thus represents crack length, while the vertical axis incorporates crack width W and delay D to display the crack size and shape.

Another feature of the invention is to detect the presence of a web edge. This is possible simply using processor 20 by assigning negative values for any channels detecting crack widths greater than 10 feet. Since such a crack is nonexisting, it is determined that the web edge lateral movement is being detected rather than an edge crack. The web edge position can therefore be determined by counting the number of channels with negative values. This technique can thus be used to detect lateral movement of the web 16. Also, as described in the aforementioned abandoned U.S. application Ser. No. 07/550,406, analog or digital filters may also be used to eliminate the effects of flutter or lateral drift.

A recording time is also used in accordance with the invention to represent the minimum amount of time that must elapse between the end of one event and the beginning of the next event, where the events occur when a crack activates at least one of the sensor channels. The recording time allows the signal processor 20 adequate time to capture the data from an event and write it to memory (disk) 22. The recording time is enforced in hardware and is dictated by the speed of the microprocessor of the signal processor 20.

Gap time, on the other hand, as used herein, is designed by software so that a typical sheet edge movement or fluttering is neglected but not an actual edge crack. This is possible since the movement or fluttering of a sheet edge position is much more frequent than the occurrance of cracks. Thus, if only one channel is activated more than once during the gap time, it is assumed to be caused by the fluttering or wandering of the sheet edge, not by an edge crack. Gap time is therefore determined by the operator, who sets the value based on experimental data of flutter and the sheet edge guiding system. The gap time is generally longer than the recording time.

As used herein, a time-out period is the maximum allowable time that an event can be recorded. It is designed so that the individual detectors can distinguish between an edge crack and the occasion when the sensor is off the edge and therefore is on continuously. The time-out period is set in software to determine the position of the edge and can be controlled by the software. Generally, the event time is longer than the gap time but shorter than the time-out period.

Figure 10B:
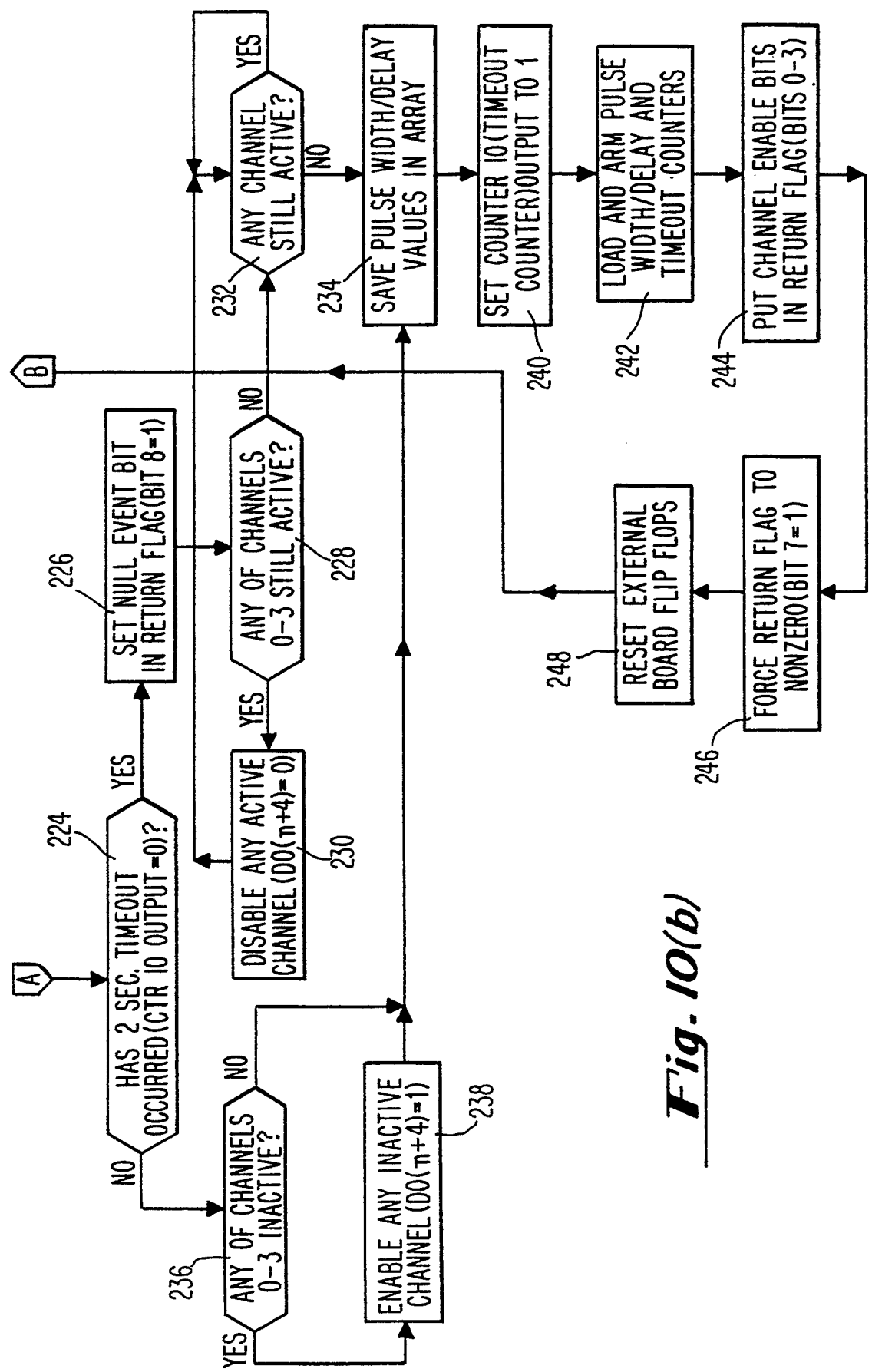

The flow chart diagrams summarizing the functioning of signal processor 20 for calculating the crack size and shape in accordance with the above-mentioned technique can be found with reference to FIGS. 9 and 10. For the purposes of this description, sensor numbering is assumed to start with 0 at the outermost sensor and end with 16 at the innermost sensor, where it is assumed that the preferred embodiment comprises 16 sensors. Only the first seven sensors (0–6) need to be used to detect the sheet edge, for it is assumed that the total lateral displacement due to sheet wandering amounts to only 1.5 inches in the direction transverse to the moving direction of the web.

In a preferred embodiment of the invention, a counter/timer board having at least 40 counters is used. Counters 1 and 2 are cascaded to form a 32-bit time stamp counter. The time stamp indicates the time, in 0.1 msec increments, from the start of data recording. The time stamp counter runs continuously and will count for almost 5 days before reaching the maximum value ($2^{32}$) before wrapping around to zero. Counters 3 and 4 are used to compare the time out-period with a duration of an event. Counters 3 and 4 begin to count down from a value for the time-out period programmed by the operator, and if it reaches zero before an event is over, it terminates the event and considers it invalid. This technique is used to prevent indefinitely long events which correspond to sheet breaks or when a sheet edge wanders out of view of a sensor. The time-out period therefore must be set to cover the maximum detectable crack width period.

Counters 5 and 6 are for gauging the duration and the delay time of a signal of sensor 0, while counters 7 and 8 gauge the duration and the delay of sensor 1, counters 9–10 are for sensor 2, and so on, until counters 35–36, which are provided for sensor 15. Each sensor covers 0.25 inch of sheet width so that a maximum crack length of 4 inches can be monitored. Of course, the range for crack length can be increased by adding more sensor channels.

The algorithm for crack dimension and shape detection in accordance with the invention starts by asking the user for information such as the desired time-out period, gap time values, file names, and the like. The system then creates a disk file for output at step 100 and programs the counter/timer boards by programming the time stamp counter at step 102 and the time-out counter at step 104. The system then installs the interrupt routine at step 106. The interrupt routine will be described in detail below with respect to FIG. 10.

The system then waits for events to occur. The events are handled by the interrupt routine which will be described below with respect to FIG. 10. The system of FIG. 9 thus monitors the interrupt at step 108 to determine when the interrupt is done. However, if the user presses an input key at step 110 before the interrupt is completed, the interrupt is disabled at step 112, the disk file is closed at step 114 and the algorithm is exited at step 116. On the other hand, when an event occurs, the interrupt routine decides whether the event is valid, and if so, data is displayed on the screen and written to the log file for later evaluation. However, if not, the program displays a column of −1, which symbolizes an invalid event. The program then waits for the next event to occur.

The algorithm of FIG. 9 communicates with the interrupt routine of FIG. 10 through an array of bits The first element of the array is used as a return flag which the interrupt routine of FIG. 10 sets to nonzeros after each event, and the algorithm of FIG. 9 sets it to zero after capturing the data before continuing with the next task. Bit 9 is set by the interrupt routine to force the flag to nonzeros, while bit 8 is set if the event ends due to a time-out. Bits 0–6 are set to the states of sensor 0–6 at the end of each events and these states are used to indicate the edge position. The remaining elements of the array are used for temporary storing of the crack width and delay time values of each channel until the completion of an event.

After processing of the interrupt routine of FIG. 10, the program of FIG. 9 first checks if a time-out occurred at step 118. If so, the event is immediately declared invalid and the paper edge is defined as the position of the highest numbered sensor which is still activated at the end of the event. The resulting values are then displayed on the display device 24 at step 120. However, if it is determined at step 118 that no time-out occurred during processing of the interrupt routine, the event counter is incremented at step 122 and the time stamp value is checked. If the event ends after the gap time, the event is valid. However, if the event ends before the gap time, the algorithm checks the number of sensors involved in the event. If only one sensor channel is involved, that sensor channel is determined to be riding on the sheet edge, where sheet fluttering makes the sensor flicker. The event is declared invalid since no crack is involved. On the other hand, if more than one sensor channel is activated, then it is determined that a crack must be passing by, and accordingly, the event is declared to be valid.

If the event is valid, the algorithm calculates the edge positions based on the order of the channels being activated (FIG. 5). It then checks all the counter values. Some counters might have zero values if the crack width at the sensor channel is zero. In such a case, the program will set the corresponding delay time, which is a function of the degree of slanting of the crack, also to zero. The algorithm will then set all crack width and delay time to −1 for any sensor channel which is off the edge of the paper. This provides a simple visual and logical way to indicate the edge position. A value of −1 indicates that the sensor is off the edge. Finally, the algorithm of FIG. 9 increments the event counter at step 122, calculates the time stamp at step 124 and then determines whether any of the channels along the edge (channel 0–6) are disabled at step 126.

If none of these channels is disabled, the crack width and delay time values are displayed on the display screen at step 128. However, if any one of these channels is disabled, at step 130 the crack width and delay time of the disabled channel are set to −1 as noted above before the crack width and delay time values are displayed on the screen at step 128. The system then checks at step 132 whether any of the pulse widths are equal to zero, and if so, at step 134 the delay is set to zero for any channel whose pulse width is equal to zero. The system then writes all data to the log file at step 136 and then waits for the next event.

The interrupt routine of FIG. 10 is activated at step 200 at the end of each event or a two second time out. As illustrated in FIG. 10 (a), an interrupt is issued at step 202, and if it is determined at step 204 that the interrupts are not enabled, the interrupt request is cleared at step 206, the interrupts are reenabled at step 208, and the system returns from the interrupt at step 210. However, if it is determined at step 204 that the interrupts are enabled, it is then determined at step 212 whether the program is busy. If the program is busy, the return flag is set to a maximum value of 256 at step 214, and the interrupts are reenabled at step 208 before the system returns from the interrupt at step 210. However, if the program is determined not to be busy at step 212, the system first latches the time stamp counter to get a time log for the event at step 216. The system then gets the current states of sensors 0–6 at step 218 for use in edge detection. The system then saves the contents of all crack width and delay times of each sensor and latches the value of the time out counter at step 220 and clears the interrupt request on the counter/timer board at step 222.

As illustrated in FIG. 10 (b), the interrupt routine next determines at step 224 whether a time out has occurred. This is indicated by the state of the output of counter 4. If the output of counter 4 is zero, it is determined that a time out occurred, and the interrupt routine communicates this fact to the program by setting bit 8 to 1 in the return flag at step 226. Otherwise, the value of bit 8 is set to zero. If a time out occurred, it is then determined at step 228 whether any of channels 0–6 are still active. If so, any active channels are disabled at step 230 until it is determined at step 232 that all of the channels are inactive. The crack width and delay time values are then stored in the array of the interrupt routine at step 234. However, if it is determined at step 224 that no time out occurred, it is determined at step 236 whether any of the channels 0–6 are inactive, and if so, any inactive channel is enabled at step 238. The counter values for crack width and the delay time values are then stored in the array of the interrupt routine at step 234.

The interrupt routine of FIG. 10 then performs housekeeping functions. Namely, it sets bit 9 in the return flag to nonzeros, updates the return flags on the states of sensors 0–6, reprograms all counters except the time stamp counter, and resets the external sensor conditioning circuit in steps 240–248. The interrupts are then reenabled at step 208 and the interrupt is exited at step 210. The crack width and delay time values can thus be formed into an image and displayed on the display screen at step 128 and stored to disk at step 136 of FIG. 9 as described above. For example, images of the type illustrated in FIGS. 6–8 will be displayed so that the severity of the crack may be determined.

Signal processor 20 may be programmed to take all values of Ps, Ds, and the number of activated channels to redisplay the crack dimensions and shapes. Preferably, signal processor 20 is capable of sorting the sensor outputs to rank cracks according to size, time of occurrence, and frequency of occurrence. Some simple statistics such as mean and standard deviation preferably can also be performed in accordance with conventional techniques Obviously, numerous modifications may be made to the invention by those skilled in the art without departing from its scope as defined in the appended claims. For example, the technique of the invention may be used to detect imperfections in fabric webs.

I claim:

1. A detector for detecting cracks on an edge of a continuous moving web, each crack having a width in a moving direction of said moving web and a length in a direction crosswise to said moving direction, said detector comprising:
   light source means for directing a plurality of beams of light toward said edge;
   light sensor means for detecting said plurality of beams of light, said light sensor means generating a plurality of detection signals dependent on respective widths of a crack at respective distances from said edge; and
   signal processing means responsive to said detection signals for determining the shape and said width and length of said crack.

2. The detector of claim 1, further comprising memory means for storing the shape, width and length of each detected crack.

3. The detector of claim 2, further comprising display means for displaying a detected crack having the determined shape, width and length.

4. The detector of claim 1, wherein said light source means comprises at least one infrared crack detection transmitter which directs a plurality of beams of infrared light toward said edge.

5. The detector of claim 4, wherein said light sensor means comprises at least one infrared crack detection receiver which receives beams of infrared light which have not been blocked by said moving web.

6. The detector of claim 5, wherein said infrared light from said light source means has a wavelength in a range of 7.5 to 9 $\mu$m.

7. The detector of claim 5, wherein each of said infrared crack detection transmitters and receivers comprises a plurality of fiber optic cables spaced in parallel a first predetermined distance apart in said direction crosswise to said moving direction, each of said infrared crack detection transmitters cooperating with a corresponding infrared crack detection receiver to monitor the presence of and width of an edge crack at a second predetermined distance from said edge.

8. The detector of claim 7, wherein each of said infrared crack detection receivers has a response time approximately equal to 0.1 ms.

9. The detector of claim 1, wherein said signal processing means comprises means for tracking said detection signals by counting a detection time interval during which light is detected by each sensor element of said light sensor means, said detection time interval being converted by said signal processing means into said crack width.

10. The detector of claim 9, wherein said signal processing means determines respective delay times for each sensor element of said light sensor means, each delay time being defined as a time duration from a predetermined point in time to a time at which a corresponding sensor element detects light, said processing means further determining said crack shape as a function of the delay time and detection time interval for each sensor element of said light sensor means.

11. The detector of claim 1, wherein said signal processing means assigns edge values to respective detection signals when a crack width greater than a predetermined width is detected, whereby a web edge position can be determined in accordance with a number of sensors of said light sensor means having said edge values.

12. The detector of claim 1, wherein said signal processing means sorts outputs of respective sensors of said light sensor means according to at least one of detected crack size, time of occurrence of each crack and frequency of occurrence of each crack.

13. A method of detecting cracks on an edge of a continuous moving web, each crack having a width in a moving direction of said moving web and a length in a direction crosswise to said moving direction, said method comprising the steps of:
   directing a plurality of beams of light toward said edge;
   detecting said plurality of beams of light using respective sensor elements of light sensor means, and in response thereto generating a plurality of detection signals dependent on respective widths of a crack at respective distances from said edge; and
   determining from said detection signals the shape and said width and length of said crack.

14. The method of claim 13, comprising the further step of storing the shape, width and length of each detected crack.

15. The method of claim 14, comprising the further step of displaying a detected crack having the determined shape, width and length.

16. The method of claim 13, comprising the further steps of tracking said detection signals by counting a detection time interval during which light is detected by each sensor element of said light sensor means and converting said detection time interval into said crack width.

17. The method of claim 16, comprising the further steps of determining respective delay times for each sensor element of said light sensor means, each delay time being defined as a time duration from a predetermined point in time to a time at which a corresponding sensor element detects light, and determining said crack shape as a function of the delay time and detection time interval for each sensor element of said light sensor means.

18. The method of claim 13, comprising the further steps of assigning edge values to respective detection signals when a crack width greater than a predetermined width is detected and determining a web edge position in accordance with a number of sensors of said light sensor means having said edge values.

19. The method of claim 13, comprising the further step of sorting outputs of respective sensors of said light sensor means according to at least one of detected crack size, time of occurrence of each crack and frequency of occurrence of each crack.

20. A detector for detecting cracks on an edge of a continuous moving web, each crack having a width in a moving direction of said moving web and a length in a direction crosswise to said moving direction, said detector comprising:
light source means for directing a plurality of beams of light toward said edge;
light sensor means having sensor elements for detecting said plurality of beams of light, said light sensor means generating a plurality of detection signals dependent on respective widths of a crack at respective distances from said edge;
means for tracking said detection signals by counting a detection time interval during which light is detected by each sensor element of said light sensor means;
means for determining respective delay times for each sensor element of said light sensor means, each delay time being defined as a time duration from a predetermined point in time to a time at which a corresponding sensor element detects light; and
processing means for determining a length of said crack from a number of sensor elements which generate a detection signal, for converting said detection time interval into a width of said crack, and for determining the shape of an irregularly shaped crack as a function of the delay time and detection time interval for each sensor element of said light sensor means.

21. A method of detecting cracks on an edge of a continuous moving web, each said crack having a width in a moving direction of said moving web and a length in a direction crosswise to said moving direction, said method comprising the steps of:
directing a plurality of beams of light toward said edge;
detecting said plurality of beams of light using respective sensor elements of light sensor means, and in response thereto generating a plurality of detection signals dependent on respective widths of a crack at respective distances from said edge;
tracking said detection signals by counting a detection time interval during which light is detected by each sensor element of said light sensor means;
determining respective delay times for each sensor element of said light sensor means, each delay time being defined as a time duration from a predetermined point in time to a time at which a corresponding sensor element detects light;
determining a length of said crack from a number of sensor elements which generate a detection signal;
converting said detection time interval into a width of said crack; and
determining the shape of an irregularly shaped crack as a function of the delay time and detection time interval for each sensor element of said light sensor means.

22. A detector for detecting cracks on an edge of a continuous moving paper web output by a papermaking machine, each crack having a width in a moving direction of said moving web and a length in a direction crosswise to said moving direction, said detector comprising:
light source means for directing a plurality of beams of light toward said edge of said paper web;
light sensor means for detecting said plurality of beams of light, said light sensor means generating a plurality of detection signals dependent on respective widths of a crack at respective distances from said edge of said paper web; and
signal processing means responsive to said detection signals for determining the shape and said width and length of said crack.

23. A method of detecting cracks on an edge of a continuous moving paper web output by a papermaking machine, each crack having a width in a moving direction of said moving web and a length in a direction crosswise to said moving direction, said method comprising the steps of:
directing a plurality of beams of light toward said edge of said paper web;
detecting said plurality of beams of light using respective sensor elements of light sensor means, and in response thereto generating a plurality of detection signals dependent on respective widths of a crack at respective distances from said edge of said paper web; and
determining from said detection signals the shape and said width and length of said crack.

24. A portable edge detector for detecting an edge of a continuous moving paper web output by a papermaking machine, said detector comprising:
a plurality of light sources for directing beams of light toward said edge;
a plurality of light sensors which detect beams of light from corresponding light sources, each light sensor generating a detection signal indicating whether a path between said light sensor and its corresponding light source is blocked by said paper web; and
signal processing means responsive to said detection signals for determining that a light sensor is beyond the edge of said paper web in accordance with whether said light sensor detects light for more than a predetermined amount of time, and for determining that said light sensor is at the edge of said paper web in accordance with whether said light sensor detects light on two or more different occasions during a gap time having a short duration during which the detection of light by said light sensor may be assumed to be caused by fluttering or wandering of the sheet edge instead of one or more cracks in said edge of said paper web.

25. A portable edge detector as in claim 24, wherein said signal processing means comprises filter means for substantially eliminating the effects of fluttering and wandering of said edge of said paper web in an output of a light sensor determined by said signal processing means to be at said edge of said paper web.

26. A method of detecting an edge of a continuous moving paper web output by a papermaking machine, said method comprising the steps of:

directing beams of light toward said edge of said paper web;

detecting beams of light received by light sensors having corresponding light sources, and each light sensor generating a detection signal indicating whether a path between said light sensor and its corresponding light source is blocked by said paper web;

determining that a light sensor is beyond the edge of said paper web in accordance with whether said light sensor detects light for more than a predetermined amount of time; and determining that said light sensor is at the edge of said paper web in accordance with whether said light sensor detects light on two or more different occasions during a gap time having a short duration during which the detection of light by said light sensor may be assumed to be caused by fluttering or wandering of the sheet edge instead of one or more cracks in said edge of said paper web.

27. A method as in claim 26, comprising the further step of substantially eliminating the effects of fluttering and wandering of said edge of said paper web in an output of a light sensor determined to be at said edge of said paper web.

* * * * *